(12) United States Patent
Cheng et al.

(10) Patent No.: US 8,329,956 B2
(45) Date of Patent: *Dec. 11, 2012

(54) PROCESS FOR PRODUCING CYCLOHEXYLBENZENE

(75) Inventors: Jane C. Cheng, Bridgewater, NJ (US); Tan-Jen Chen, Kingwood, TX (US); Prasenjeet Ghosh, Annandale, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/409,331

(22) Filed: Mar. 1, 2012

(65) Prior Publication Data
US 2012/0178969 A1 Jul. 12, 2012

Related U.S. Application Data

(63) Continuation of application No. 12/920,383, filed as application No. PCT/US2009/034976 on Feb. 24, 2009, now Pat. No. 8,178,728.

(60) Provisional application No. 61/044,678, filed on Apr. 14, 2008.

(51) Int. Cl.
C07C 45/27 (2006.01)
C07C 27/08 (2006.01)
C07C 2/68 (2006.01)
C07C 15/067 (2006.01)

(52) U.S. Cl. ........ 568/361; 568/798; 585/266; 585/268; 585/467

(58) Field of Classification Search .......... 568/361, 568/798; 585/266, 268, 467
See application file for complete search history.

(56) References Cited

U.S. PATENT DOCUMENTS

| | | |
|---|---|---|
| 3,197,399 A | 7/1965 | Wight et al. |
| 3,201,356 A | 8/1965 | Kress et al. |
| 3,347,945 A | 10/1967 | Slaugh |
| 3,390,101 A | 6/1968 | Csicsery |
| 3,412,165 A | 11/1968 | Slaugh et al. |
| 3,536,771 A | 10/1970 | Graff |
| 3,760,017 A | 9/1973 | Arkell et al. |
| 3,760,018 A | 9/1973 | Suggitt et al. |
| 3,760,019 A | 9/1973 | Crone, Jr. et al. |
| 3,784,617 A | 1/1974 | Suggitt et al. |
| 3,784,618 A | 1/1974 | Suggitt et al. |
| 3,839,477 A | 10/1974 | Suggitt et al. |
| 3,864,421 A | 2/1975 | Suggitt |
| 3,957,687 A | 5/1976 | Arkell et al. |
| 3,962,362 A | 6/1976 | Suggitt |
| 4,021,490 A | 5/1977 | Hudson |
| 4,094,918 A | 6/1978 | Murtha et al. |
| 4,122,125 A | 10/1978 | Murtha et al. |
| 4,152,362 A | 5/1979 | Murtha |
| 4,177,165 A | 12/1979 | Murtha et al. |
| 4,206,082 A | 6/1980 | Murtha et al. |
| 4,219,689 A | 8/1980 | Murtha |
| 4,268,699 A | 5/1981 | Murtha et al. |
| 4,329,531 A | 5/1982 | Murtha et al. |
| 4,380,683 A | 4/1983 | Dolhyj et al. |
| 4,439,409 A | 3/1984 | Puppe et al. |
| 4,447,554 A | 5/1984 | Murtha et al. |
| 4,826,667 A | 5/1989 | Zones et al. |
| 4,954,325 A | 9/1990 | Rubin et al. |
| 4,962,250 A | 10/1990 | Dessau et al. |
| 5,037,538 A | 8/1991 | Chin et al. |
| 5,053,571 A | 10/1991 | Makkee |
| 5,108,969 A | 4/1992 | Del Rossi et al. |
| 5,146,024 A | 9/1992 | Reed |
| 5,236,575 A | 8/1993 | Bennett et al. |
| 5,250,277 A | 10/1993 | Kresge et al. |
| 5,292,976 A | 3/1994 | Dessau et al. |
| 5,326,697 A | 7/1994 | Magers |
| 5,334,795 A | 8/1994 | Chu et al. |
| 5,362,697 A | 11/1994 | Fung et al. |
| 5,384,296 A | 1/1995 | Tsao |
| 5,488,194 A | 1/1996 | Beck et al. |
| 5,554,274 A | 9/1996 | Degnan et al. |
| 5,557,024 A | 9/1996 | Cheng et al. |
| 5,705,729 A | 1/1998 | Huang |
| 6,037,513 A | 3/2000 | Chang et al. |
| 6,077,498 A | 6/2000 | Diaz Cabanas et al. |
| 6,133,470 A | 10/2000 | Beck et al. |
| 6,489,529 B1 | 12/2002 | Cheng et al. |
| 6,504,070 B2 | 1/2003 | Matsumoto et al. |

(Continued)

FOREIGN PATENT DOCUMENTS

| | | |
|---|---|---|
| EP | 0 293 032 | 11/1988 |
| EP | 0 338 734 | 10/1989 |
| JP | 2005-342644 | 12/2005 |
| WO | 95/31421 | 11/1995 |
| WO | 97/17290 | 5/1997 |
| WO | 01/53236 | 7/2001 |
| WO | 01/74767 | 11/2001 |
| WO | 2005/118476 | 12/2005 |
| WO | 2009/038900 | 3/2009 |
| WO | 2009/131769 | 10/2009 |

OTHER PUBLICATIONS

Borodina, I.B. et al., "Hydroalkylation of Benzene and Ethylbenzene over Metal Containing Zeolite Catalysts", Microporous and Mesoporous Materials, 2007, vol. 105, pp. 181-188.

(Continued)

Primary Examiner — Sikarl Witherspoon
(74) Attorney, Agent, or Firm — Anthony G. Boone; Jamie L. Sullivan; Siwen Chen

(57) ABSTRACT

In a process for producing cyclohexylbenzene, benzene and hydrogen are contacted under hydroalkylation conditions with a catalyst system comprising a MCM-22 family molecular sieve and at least one hydrogenation metal. The conditions comprise a temperature of about 140° C. to about 175° C., a pressure of about 135 psig to about 175 psig (931 kPag to 1207 kPag), a hydrogen to benzene molar ratio of about 0.30 to about 0.65 and a weight hourly space velocity of benzene of about 0.26 to about 1.05 hr$^{-1}$.

21 Claims, 4 Drawing Sheets

U.S. PATENT DOCUMENTS

| | | | |
|---|---|---|---|
| 6,506,953 | B1 | 1/2003 | Cheng et al. |
| 6,730,625 | B1 | 5/2004 | Chang et al. |
| 6,781,025 | B2 | 8/2004 | Dandekar et al. |
| 6,936,744 | B1 | 8/2005 | Cheng et al. |
| 7,488,861 | B2 | 2/2009 | Boyer et al. |
| 7,579,511 | B1 | 8/2009 | Dakka et al. |
| 2003/0083527 | A1 | 5/2003 | Kuhnle et al. |
| 2004/0092757 | A1 | 5/2004 | Oguchi et al. |
| 2005/0158238 | A1 | 7/2005 | Tatsumi et al. |
| 2008/0027256 | A1 | 1/2008 | Roth et al. |
| 2008/0027259 | A1 | 1/2008 | Roth et al. |
| 2008/0045768 | A1 | 2/2008 | Roth et al. |
| 2011/0037022 | A1 | 2/2011 | Dakka et al. |

OTHER PUBLICATIONS

Fan, W. et al. "Synthesis and Catalytic Properties of a New Titanosilicate Molecular Sieve with the Structure Analogous to MWW-type Lamellar Precursor" Journal of Catalyst, 2006, vol. 243, pp. 183-191.

Lawton, S.L. et al. "Zeolite MCM-49: A Three-Dimensional MCM-22 Analogue Synthesized by in Situ Crystallization", Journal of Physical Chemistry, 1996, vol. 100, No. 9, pp. 3788-3798.

Maheshwari, S. et al., "Layer Structure Preservation During Swelling, Pillaring, and Exfoliation of a Zeolite Precursor" Journal of American Chemical Soc., 2008, vol. 130, No. 4, pp. 1507-1516.

Ruan, J. "Structure Elucidation of the Highly Active Titanosilicate Catalyst Ti-YNU-1" Angew. Chem. Int. Ed., 2005, vol. 44, pp. 6719-6723.

Se-Young, K. et al., "Structural Evolution of B-MCM-36 and B-ITQ-2 from B-MCM-22" Bull. Korean Chem. Society, 2006, vol. 27, No. 10, pp. 1693-1696.

Slaugh, L.H. et al., "Hydrodimerization of Benzene to Phenylcyclohexane over Supported Transition Metal Catalysts" Journal of Catalysis, 1969, vol. 13, pp. 385-396.

Wu, P. et al., "Methodology for Synthesizing Crystalline Metallosilicates with Expanded Pore Windows Through Molecular Alkoxysilylation of Zeolitic Lamellar Precursors" Journal of American Chemical Soc., 2008, vol. 130, pp. 8178-8187.

Zhicheng L. et al, "Static Synthesis of High-Quality MCM-22 Zeolite with High $SiO_2/Al_2O_3$ Ratio" Chinese Science Bull, 2004, vol. 49, No. 6, pp. 556-561.

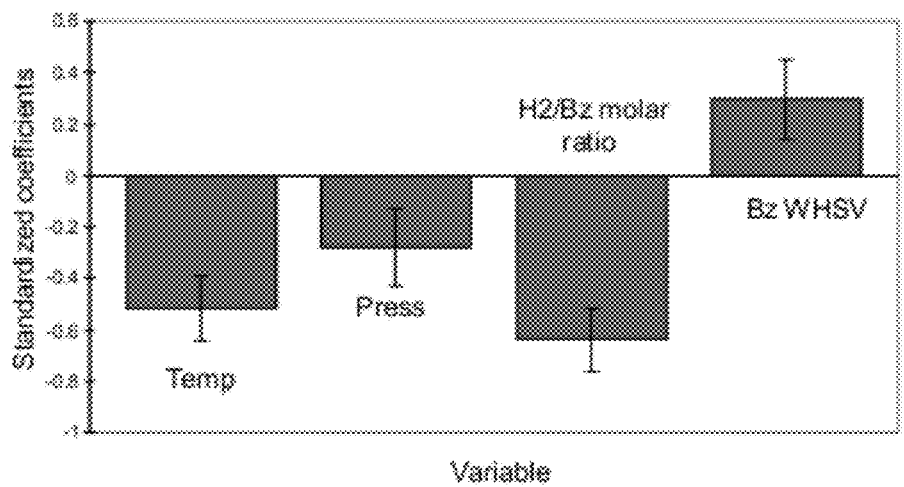
FIGURE I (C)
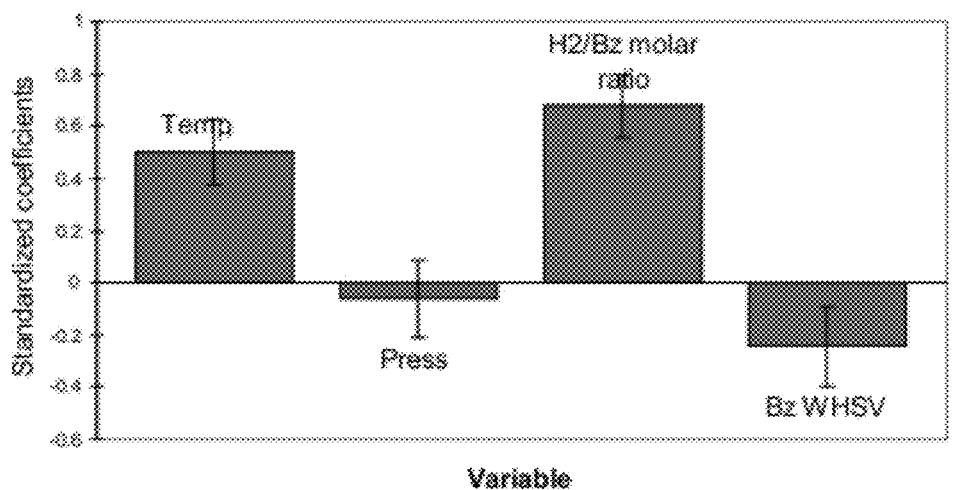
FIGURE I (D)

PROCESS FOR PRODUCING CYCLOHEXYLBENZENE

PRIORITY CLAIM

This application is a continuation of and claims priority to U.S. application Ser. No. 12/920,383 filed Aug. 31, 2010, now U.S. Pat. No. 8,178,728 which claims priority to National Stage Application of International Application No. PCT/US2009/034976 filed Feb. 24, 2009, which claims priority from U.S. Ser. No. 61/044,678 filed Apr. 14, 2008, all of which are incorporated herein by reference in their entirety.

FIELD OF THE INVENTION

The present invention relates to a process for producing cyclohexylbenzene and optionally for converting the resultant cyclohexylbenzene into phenol and cyclohexanone.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene. Thus, a process that uses higher alkenes instead of propylene as feed and coproduces higher ketones, rather than acetone, may be an attractive alternative route to the production of phenols.

For example, oxidation of cyclohexylbenzene (analogous to cumene oxidation) could offer an alternative route for phenol production without the problem of acetone co-production. This alternative route co-produces cyclohexanone, which has a growing market and is used as an industrial solvent, as an activator in oxidation reactions and in the production of adipic acid, cyclohexanone resins, cyclohexanone oxime, caprolactam and nylon 6. However, this alternative route requires the development of a commercially viable process for producing the cyclohexylbenzene precursor.

It has been known for many years that cyclohexylbenzene can be produced from benzene by the process of hydroalkylation or reductive alkylation. In this process, benzene is reacted with hydrogen in the presence of a catalyst such that the benzene undergoes partial hydrogenation to produce cyclohexene which then alkylates the benzene starting material. Thus U.S. Pat. Nos. 4,094,918 and 4,177,165 disclose hydroalkylation of aromatic hydrocarbons over catalysts which comprise nickel- and rare earth-treated zeolites and a palladium promoter. Similarly, U.S. Pat. Nos. 4,122,125 and 4,206,082 disclose the use of ruthenium and nickel compounds supported on rare earth-treated zeolites as aromatic hydroalkylation catalysts. The zeolites employed in these prior art processes are zeolites X and Y. In addition, U.S. Pat. No. 5,053,571 proposes the use of ruthenium and nickel supported on zeolite beta as the aromatic hydroalkylation catalyst. However, these earlier proposals for the hydroalkylation of benzene suffer from the problems that the selectivity to cyclohexylbenzene is low, particularly at economically viable benzene conversion rates, and that large quantities of unwanted by-products are produced.

More recently, U.S. Pat. No. 6,037,513 has disclosed that cyclohexylbenzene selectivity in the hydroalkylation of benzene can be improved by contacting the benzene and hydrogen with a bifunctional catalyst comprising at least one hydrogenation metal and a molecular sieve of the MCM-22 family. The hydrogenation metal is preferably selected from palladium, ruthenium, nickel, cobalt and mixtures thereof and the contacting step is conducted at a temperature of about 50 to 350° C., a pressure of about 100 to 7000 kPa, a benzene to hydrogen molar ratio of about 0.01 to 100 and a WHSV of about 0.01 to 100. The '513 patent discloses that the resultant cyclohexylbenzene can then be oxidized to the corresponding hydroperoxide and the peroxide decomposed to the desired phenol and cyclohexanone.

However, despite recent advances, the hydroalkylation of benzene to produce cyclohexylbenzene has still not been commercialized. One problem is that the chemistry involved in the hydroalkylation reaction is quite complicated and tends to produce cyclohexane, methylcyclopentane, methylcyclopentylbenzene, methylcyclopentyl-cyclohexylbenzene, and dicyclohexylbenzenes in addition to the desired cyclohexylbenzene. While dicyclohexylbenzenes can be transalkylated with benzene to produce additional cyclohexylbenzene, for a commercially viable process it is necessary to minimize the production of low-value impurities that are expensive to remove and/or process. Of these impurities, methylcyclopentane and methylcyclopentylbenzene are particularly undesirable since their close boiling points (relative to cyclohexane/benzene and cyclohexylbenzene, respectively) make them very difficult to separate from cyclohexylbenzene. Moreover, although cyclohexane can be converted back to benzene by dehydrogenation, this represents a costly and circuitous path to feed retrieval.

Given these complexities, there has been a significant question as to whether the production of phenol via benzene hydroalkylation to cyclohexylbenzene could be an economically viable alternative to the conventional route via cumene. However, as a result of extensive research, a combination of catalyst composition and process parameters has now been established that offers a benzene hydroalkylation process with a high cyclohexylbenzene yield coupled with a low production of undesirable impurities.

SUMMARY

In one aspect, the invention resides in a process for producing cyclohexylbenzene, the process comprising contacting benzene and hydrogen under hydroalkylation conditions with a catalyst system comprising a MCM-22 family molecular sieve and at least one hydrogenation metal, wherein said conditions comprise a temperature of about 140° C. to about 175° C., a pressure of about 135 psig to about 175 psig (931 kPag, 1032 kPa to 1207 kPag, 1308 kPa), a hydrogen to benzene molar ratio of about 0.30 to about 0.65 and a weight hourly space velocity of benzene of about 0.26 to about 1.05 $hr^{-1}$.

Conveniently, said conditions comprise a temperature of about 150° C. to about 160° C. and/or a pressure of about 145 psig to about 155 psig (1000 kPag to 1069 kPag) and/or a hydrogen to benzene molar ratio of about 0.45 to about 0.64 and/or a weight hourly space velocity of benzene of about 0.3 to about 0.6 $hr^{-1}$.

Conveniently, said MCM-22 family molecular sieve has an X-ray diffraction pattern including d-spacing maxima at 12.4±0.25, 6.9±0.15, 3.57±0.07 and 3.42±0.07 Angstrom. In one embodiment, the MCM-22 family molecular sieve is selected from MCM-22, PSH-3, SSZ-25, ERB-1, ITQ-1, ITQ-2, MCM-36, MCM-49, MCM-56, UZM-8, and mixtures of any two or more thereof, especially from MCM-22, MCM-49, MCM-56 and combinations of any two or more thereof.

Conveniently, said at least one hydrogenation metal is selected from palladium, ruthenium, nickel, zinc, tin and cobalt, and preferably is palladium. Generally, said at least one hydrogenation metal is present in an amount between about 0.05 and about 10%, such as between about 0.1 and about 5%, by weight of the catalyst system.

In one embodiment, at least 50 wt %, such as at least 75 wt %, and preferably substantially all such as greater than 95, 98 or 99 wt % of said hydrogenation metal is supported on an inorganic oxide that is different from said molecular sieve. Conveniently, the inorganic oxide comprises an oxide of at least one element selected from Groups 2, 4, 13 and 14 of the Periodic Table of Elements, such as alumina and/or titania and/or zirconia.

In a further aspect, the invention resides in a method for coproducing phenol and cyclohexanone, the method comprising producing cyclohexylbenzene by the process described herein, oxidizing the cyclohexylbenzene to produce cyclohexylbenzene hydroperoxide and cleaving the cyclohexylbenzene hydroperoxide to produce phenol and cyclohexanone. In a preferred embodiment, the method further comprises dehydrogenating the cyclohexane to produce further phenol.

DETAILED DESCRIPTION OF THE EMBODIMENTS

Figure 1:
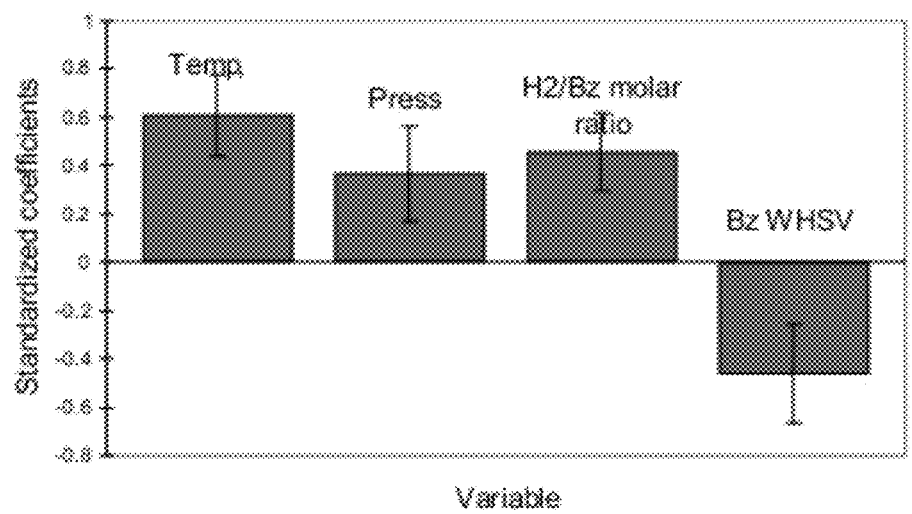
FIGS. 1(a) to (d) are graphs plotting the effect of the process variables temperature, pressure, hydrogen to benzene molar ratio and weight hourly space velocity of benzene on the weight % benzene conversion (FIG. 1(a)), cyclohexane (CH) selectivity (FIG. 1(b)), cyclohexylbenzene (CHB) selectivity (FIG. 1(c)), and dicyclohexylbenzene (DCHB) selectivity (FIG. 1(d)).
Figure 1:
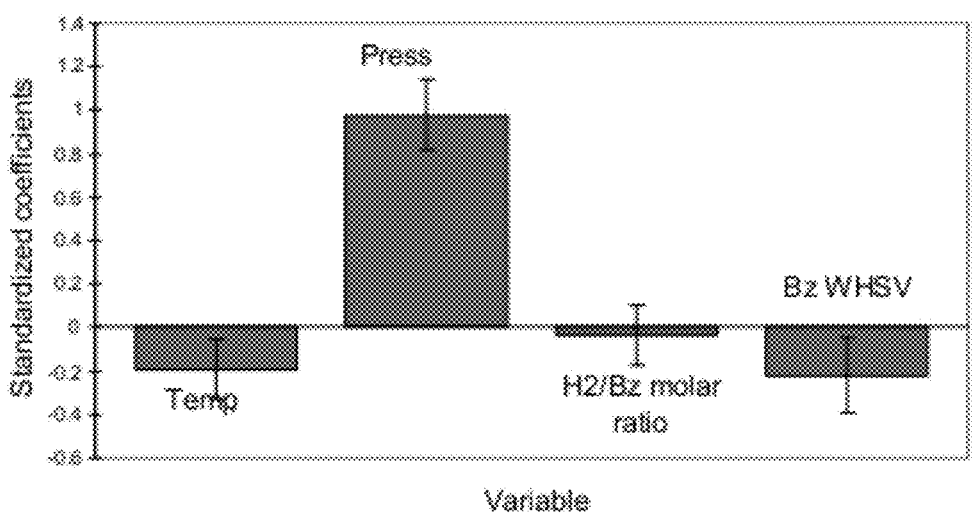

Described herein is a process for the hydroalkylation of benzene to produce cyclohexylbenzene and, in a preferred embodiment of the invention, the conversion of the cyclohexylbenzene in a second step to cyclohexanone and phenol. Insofar as the hydroalkylation process produces dicyclohexylbenzene in addition to the desired monocyclohexylbenzene product, the process can include the further step of transalkylating the dicyclohexylbenzene with additional benzene to produce additional monocyclohexylbenzene product.

Benzene Hydroalkylation

The present process (which comprises the first process step in the above-mentioned preferred embodiment) comprises contacting benzene with hydrogen under hydroalkylation conditions in the presence of a hydroalkylation catalyst whereby the benzene undergoes the following partial hydrogenation/alkylation reaction to produce cyclohexylbenzene (CHB):

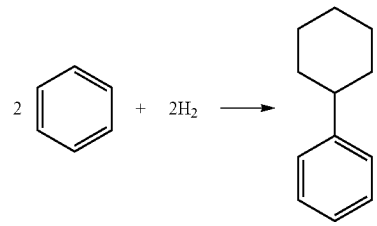

Competing reactions include the complete saturation of the benzene to produce cyclohexane (CH), dialkylation to produce dicyclohexylbenzene (DCHB) and reorganization/alkylation reactions to produce impurities, such as methylcyclopentane (MCP), methylcyclopentylbenzene (MCPB), and methylcyclopentyl-cyclohexylbenzene (MCPCHB). Although dicyclohexylbenzene can be transalkylated to produce additional CHB product, conversion to cyclohexane represents loss of valuable feed, whereas impurities such as methylcyclopentane (MCP) and methylcyclopentylbenzene (MCPB) are particularly undesirable since their boiling points are very close to that of CHB so that it is very difficult to separate MCP and MCPB from CHB. It is therefore important to minimize the production of DCHB, MCP and MCPB impurities in the hydroalkylation reaction, so that the concentrations of such materials in the hydroalkylation product mixture (also termed herein the hydroalkylation effluent) are kept to acceptably low levels.

According to the present invention, there is provided an optimized benzene hydroalkylation process which is effective to convert benzene to cyclohexylbenzene (CHB) with high selectivity and at high yield, and in which the production of cyclohexane is preferably less than or equal to 3 wt % of the total hydroalkylation effluent and/or the production of MCP, MCPB and MCPCHB in combination is preferably less than or equal to 5 wt % of the total hydroalkylation effluent. Typically, the production of dicyclohexylbenzene (DCHB) is less than 15 wt % of the total hydroalkylation effluent.

Any commercially available benzene feed can be used in the present hydroalkylation process, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm by weight, water and/or less than 100 ppm, such as less than 30 ppm, for example less than 3 ppm by weight, sulfur and/or less than 10 ppm, such as less than 1 ppm, for example less than 0.1 ppm by weight, nitrogen.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Irrespective of whether the hydrogen is fed to the reaction continuously or in stages, it is important that the ratio of the total number of moles of hydrogen fed to the reaction to the number of moles of benzene fed to the reaction is between 0.30:1 and 0.65:1, such as between about 0.45:1 and about 0.64:1. In particular, as will be come apparent from the ensuing Example, controlling the hydrogen to benzene molar ratio within these limits maximizes the yield of cyclohexylbenzene without significantly increasing the yield of dicyclohexylbenzene.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques such as using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures of any two or more thereof. Preferably, the molecular sieve is selected from (a) MCM-49, (b) MCM-56 and (c) isotypes of MCM-49 and MCM-56, such as ITQ-2.

Any known hydrogenation metal can be employed in the present hydroalkylation catalyst although suitable metals include palladium, ruthenium, nickel, zinc, tin and cobalt, with palladium being particularly advantageous. Generally, the amount of hydrogenation metal present in the catalyst is preferred to be between about 0.05 and about 10 wt %, such as between about 0.1 and about 5 wt %, of the catalyst system. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75wt %, and particularly preferably substantially all e.g. at least 95, 98 or 99 wt % of the hydrogenation metal is supported on an inorganic oxide separate (i.e. different) from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Whether a separate inorganic oxide is used with the molecular sieve or not, the catalyst system may additionally be combined with a binder to facilitate its use in the process of the invention. Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia and silica-titania as well as ternary compositions such as silica-alumina-thoria, silica-alumina-zirconia, silica-alumina-magnesia and silica-magnesia-zirconia.

The conditions employed in the present process are important in achieving the desired selectivity to cyclohexylbenzene and include a temperature of about 140° C. to about 175° C., particularly about 150° C. to about 160° C., a pressure of about 931 kPag to 1207 kPag (135 psig to about 175 psig), particularly about 1000 kPag to 1069 kPag (145 psig to about 155 psig), a hydrogen to benzene molar ratio of about 0.30 to about 0.65, particularly about 0.45 to about 0.64, and a weight hourly space velocity of benzene of about 0.26 to about 1.05 $hr^{-1}$, particularly about 0.3 to about 0.6 $hr^{-1}$.

Using these conditions and an MCM-22 family zeolite, the present hydroalkylation process is effective to convert benzene to the product mix shown in Table 1 below (% by weight).

TABLE 1

|  | Preferred Range | More Preferred Range |
|---|---|---|
| Benzene Conversion | 30-55% | 40-50% |
| CHB Yield | 25-40% | 30-35% |
| DCHB Yield | 5-13% | 6-9% |
| Cyclohexane Yield | 1.0-2.5% | 1.5-2.0% |
| Other Byproducts Yield (including MCP, MCPB, MCP-CHB) | 1.5-4.0% | 1.8-2.5% |
| MCP Yield | 0.04-0.2% | 0.045-0.1% |
| MCPB Yield | 0.7-1.2% | 0.8-1% |
| MCP-CHB Yield | 0.5-1.5% | 0.6-1.4% |

Dicyclohexylbenzene Transalkylation

Although the hydroalkylation step is highly selective towards cyclohexylbenzene, it will be seen from Table 1 that the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to transalkylate the dicyclohexylbenzene with additional benzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y or mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 hr−1 on total feed, and a benzene/dicyclohexylbenzene weight ratio about of 1:1 to about 5:1.

Cyclohexylbenzene Oxidation

In a preferred embodiment, the cyclohexylbenzene produced by the process of that invention is further converted. Thus, in order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2dicarboximide, N-hydroxynaphthalimide sodium salt or N-hydroxy-o-benzene-disulphonimide. Preferably, the catalyst is N-hydroxyphthalimide. Another suitable catalyst is N,N',N"-trihydroxyisocyanuric acid.

These catalytic materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount of from 0.0001 wt % to 15 wt %, such as from 0.001 to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., and/or a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

The crude cyclohexanone and crude phenol from the cleavage step may be subjected to further purification to produce purified cyclohexanone and phenol. A suitable purification process includes, but is not limited to, a series of distillation towers to separate the cyclohexanone and phenol from other species. The crude or purified cyclohexanone may itself be subjected to dehydrogenation in order to convert it to phenol. Such dehydrogenation may be performed, for example, over a catalyst such as platinum, nickel or palladium.

The following Examples are given for illustrative purposes and do not limit the scope of the invention.

EXAMPLE 1

Catalyst Preparation

A catalyst was prepared by co-pelletizing a Pd catalyst with a MCM-49 catalyst. The Pd catalyst was prepared by impregnating 5 grams of gamma alumina with a palladium nitrate solution and then calcining the Pd impregnated alumina at 350° C. for 3 hours in air. The Pd loading on the alumina was 0.3 wt %. The MCM-49 catalyst was prepared by crushing an extrudate which had 80 wt % MCM-49 and 20 wt % alumina to 0.042 cm (1/60") or finer particles. The Pd/Al$_2$O$_3$ catalyst was then mixed with the crushed MCM-49/Al$_2$O$_3$ in the ratio of 1:3 by weight and then pelletized using a hand press under 138 MPag (20,000 psig) to form the co-pelletized catalyst. The catalyst was then sized to mesh openings of from 0.250 mm to 0.149 mm (60-100 mesh) for testing.

EXAMPLE 2

Benzene Hydroalkylation

Eight grams of the catalyst prepared in Example 1 was charged to a stainless steel fixed-bed micro-reactor. The reactor had a 1.27 cm (½ inch) inside diameter with a 0.32 cm (⅛ inch) thermowell in the center throughout the catalyst bed. The catalyst was pretreated with 100 cc/min of hydrogen for 2 hours at 300° C. and 1 atm. After cooling to 155° C. in hydrogen, benzene was fed into the reactor through a syringe pump at 60 cc/hour for 1 hr while the reactor pressure was increased to 1034 kPag (150 psig). The benzene feed rate was then reduced to 0.52 WHSV and the hydrogen/benzene molar ratio was adjusted to 1.28. Liquid products were collected in a cold product trap and analyzed off-line. Various test conditions were used to evaluate catalyst performance by varying four process variables. Table 2 shows these process variables and their ranges. A total of 36 test conditions were used to study CHB production.

TABLE 2

| Variable | Total Conditions | Minimum | Maximum | Mean | Std. deviation |
|---|---|---|---|---|---|
| Temperature, ° C. | 36 | 125 | 175 | 148.28 | 13.40 |
| Pressure, kPag | 36 | 862 | 4137 | 1796 | 1141 |
| Pressure, psig | 36 | 125 | 600 | 260.56 | 165.55 |
| H2/Benzene Molar Ratio | 36 | 0.32 | 1.28 | 0.76 | 0.33 |
| Benzene WHSV | 36 | 0.26 | 1.05 | 0.60 | 0.24 |

Results of catalyst performance are shown in Tables 3 to 6, in which CHB represents cyclohexylbenzene, DCHB represents dicyclohexylbenzene, MCPB represents methylcyclopentylbenzene and MCP-CHB represents methylcyclopentyl-cyclohexylbenzene, Table 3 shows test results obtained under test condition 1 to condition 10; and Tables 4, 5 and 6 show test results obtained under test conditions 11 to 19, 20 to 28 and 29 to 36, respectively.

TABLE 3

| Test Condition No. | 1 | 2 | 3 | 4 | 5 | 6 | 7 | 8 | 9 | 10 |
|---|---|---|---|---|---|---|---|---|---|---|
| Temperature, ° C. | 150 | 150 | 150 | 125 | 125 | 150 | 150 | 150 | 150 | 138 |
| Pressure, kPag | 1034 | 1034 | 1034 | 1207 | 1207 | 862 | 862 | 1207 | 1207 | 1034 |
| Pressure, psig | 150 | 150 | 150 | 175 | 175 | 125 | 125 | 175 | 175 | 150 |
| H2/Benzene Molar Ratio | 0.45 | 0.63 | 1.00 | 0.46 | 0.63 | 0.45 | 0.63 | 0.45 | 0.63 | 0.63 |
| Benzene WHSV | 0.52 | 0.52 | 0.52 | 0.52 | 0.52 | 0.52 | 0.52 | 0.52 | 0.52 | 0.52 |
| Benzene Conv, % | 37.5 | 43.1 | 47.6 | 24.0 | 24.9 | 36.7 | 36.2 | 38.9 | 49.5 | 32.6 |
| Selectivity, wt % | | | | | | | | | | |
| Cyclohexane | 4.0 | 4.5 | 4.8 | 7.6 | 7.6 | 4.8 | 3.7 | 5.4 | 5.1 | 5.4 |
| CHB | 79.0 | 72.5 | 63.8 | 82.4 | 81.5 | 77.7 | 73.0 | 78.0 | 71.8 | 78.9 |
| DCHB | 13.2 | 18.5 | 24.3 | 8.3 | 6.5 | 13.8 | 18.2 | 13.1 | 17.3 | 12.8 |
| Others | 3.8 | 4.5 | 7.1 | 1.7 | 4.5 | 3.7 | 5.1 | 3.5 | 5.8 | 2.9 |
| Sum | 100 | 100 | 100 | 100 | 100 | 100 | 100 | 100 | 100 | 100 |
| CHB + DCHB | 92.2 | 91.0 | 88.1 | 90.7 | 88.0 | 91.5 | 91.2 | 91.1 | 89.1 | 91.7 |
| Product Yield, % | | | | | | | | | | |
| Cyclohexane | 1.5 | 1.9 | 2.3 | 1.8 | 1.9 | 1.8 | 1.3 | 2.1 | 2.5 | 1.8 |
| CHB | 29.6 | 31.2 | 30.4 | 19.8 | 20.3 | 28.5 | 26.4 | 30.3 | 35.5 | 25.7 |
| DCHB | 5.0 | 8.0 | 11.6 | 2.0 | 1.6 | 5.1 | 6.6 | 5.1 | 8.6 | 4.2 |
| CHB + DCHB | 34.6 | 39.2 | 41.9 | 21.8 | 21.9 | 33.6 | 33.0 | 35.4 | 44.1 | 29.9 |

TABLE 4

| Test Condition No. | 11 | 12 | 13 | 14 | 15 | 16 | 17 | 18 | 19 |
|---|---|---|---|---|---|---|---|---|---|
| Days on Stream | 2.7 | 5.7 | 8.7 | 12.2 | 15.7 | 23.7 | 27.7 | 28.7 | 31.2 |
| Temperature, ° C. | 150 | 150 | 150 | 150 | 150 | 150 | 150 | 150 | 150 |
| Pressure, kPag | 1138 | 2069 | 2069 | 1138 | 1034 | 1034 | 1034 | 2069 | 4137 |
| Pressure, psig | 165 | 300 | 300 | 165 | 150 | 150 | 150 | 300 | 600 |
| H2/Benzene Molar Ratio | 1.28 | 1.28 | 1.28 | 1.28 | 0.64 | 0.64 | 1.28 | 0.64 | 0.64 |
| Benzene WHSV | 0.52 | 0.52 | 1.05 | 0.26 | 0.52 | 0.26 | 0.52 | 0.52 | 1.05 |
| Benzene Conv, % | 45.7 | 68.5 | 38.1 | 68.5 | 33.6 | 41.9 | 40.6 | 53.5 | 51.6 |
| Hydrogen Conv, % | 48.6 | 75.0 | 30.4 | 98.0 | 86.8 | 97.0 | 30.6 | 97.3 | 96.5 |

TABLE 4-continued

| Test Condition No. | 11 | 12 | 13 | 14 | 15 | 16 | 17 | 18 | 19 |
|---|---|---|---|---|---|---|---|---|---|
| Selectivity, wt % | | | | | | | | | |
| Methylcyclopentane | 0.40 | 0.30 | 0.09 | 0.26 | 0.09 | 0.13 | 0.27 | 0.18 | 0.11 |
| Cyclohexane | 4.0 | 6.1 | 5.1 | 6.0 | 4.2 | 5.0 | 3.9 | 5.9 | 10.4 |
| CHB | 63.9 | 58.6 | 71.8 | 58.4 | 75.8 | 72.8 | 61.5 | 69.1 | 67.5 |
| Methylcyclopentyl-benzene | 2.5 | 2.2 | 2.0 | 2.3 | 2.1 | 2.4 | 2.5 | 2.3 | 1.9 |
| DCHB | 24.5 | 27.6 | 18.2 | 27.3 | 15.5 | 16.6 | 26.4 | 19.4 | 17.2 |
| Methylcyclopentyl-cyclohexylbenzene | 3.1 | 3.1 | 2.2 | 3.6 | 1.8 | 2.4 | 3.3 | 2.2 | 2.3 |
| Others | 1.4 | 2.0 | 0.6 | 2.1 | 0.4 | 0.4 | 1.9 | 0.7 | 0.5 |
| Sum | 100 | 100 | 100 | 100 | 100 | 100 | 100 | 100 | 100 |
| CHB + DCHB sel, % | 88.4 | 86.2 | 90.0 | 85.6 | 91.3 | 89.4 | 88.0 | 88.6 | 84.7 |
| Product Yield, % | | | | | | | | | |
| Cyclohexane | 1.8 | 3.0 | 2.5 | 2.9 | 2.0 | 2.4 | 1.9 | 2.9 | 5.1 |
| CHB | 29.2 | 28.6 | 35.0 | 28.4 | 37.0 | 35.5 | 30.0 | 33.7 | 32.9 |
| DCHB | 11.2 | 13.5 | 8.9 | 13.3 | 7.5 | 8.1 | 12.9 | 9.5 | 8.4 |
| CHB + DCHB | 40.4 | 42.0 | 43.9 | 41.7 | 44.5 | 43.6 | 42.9 | 43.2 | 41.3 |

TABLE 5

| Test Condition No. | 20 | 21 | 22 | 23 | 24 | 25 | 26 | 27 | 28 |
|---|---|---|---|---|---|---|---|---|---|
| Days on Stream | 34.7 | 36.7 | 39.6 | 41.4 | 43.7 | 56.6 | 57.8 | 61.7 | 64.7 |
| Temperature, ° C. | 150 | 150 | 175 | 175 | 150 | 150 | 125 | 125 | 150 |
| Pressure, kPag | 1034 | 2069 | 1034 | 1034 | 1034 | 2069 | 4137 | 4137 | 2069 |
| Pressure, psig | 150 | 300 | 150 | 150 | 150 | 300 | 600 | 600 | 300 |
| H2/Benzene Molar | 0.64 | 0.32 | 0.64 | 0.64 | 0.64 | 0.32 | 0.64 | 1.28 | 1.28 |
| Benzene WHSV | 0.52 | 0.52 | 1.05 | 0.52 | 0.52 | 1.05 | 1.05 | 0.52 | 0.52 |
| Benzene Conv, % | 37.6 | 28.1 | 29.5 | 53.5 | 41.8 | 28.6 | 19.6 | 37.1 | 64.4 |
| Hydrogen Conv, % | 67.8 | 96.6 | 53.9 | 96.8 | 64.9 | 95.3 | 33.7 | 32.2 | 65.0 |
| Selectivity, wt % | | | | | | | | | |
| Methylcyclopentane | 0.11 | 0.09 | 0.52 | 0.74 | 0.13 | 0.07 | 0.04 | 0.04 | 0.16 |
| Cyclohexane | 4.5 | 6.5 | 3.7 | 4.2 | 3.4 | 5.3 | 10.3 | 12.9 | 7.9 |
| CHB | 73.0 | 79.5 | 70.8 | 66.2 | 72.8 | 79.4 | 79.2 | 71.8 | 59.8 |
| MCPB | 2.1 | 2.5 | 4.3 | 4.9 | 2.3 | 2.0 | 1.1 | 1.0 | 2.0 |
| DCHB | 17.4 | 9.6 | 16.9 | 19.2 | 18.3 | 11.7 | 8.3 | 12.7 | 25.1 |
| MCP-CHB | 2.2 | 1.6 | 3.1 | 3.8 | 2.4 | 1.3 | 0.8 | 1.3 | 3.3 |
| Others | 0.5 | 0.0 | 0.6 | 0.8 | 0.6 | 0.2 | 0.0 | 0.2 | 1.6 |
| Sum | 100 | 100 | 100 | 100 | 100 | 100 | 100 | 100 | 100 |
| CHB + DCHB sel, % | 90.4 | 89.1 | 87.7 | 85.4 | 91.1 | 91.1 | 87.5 | 84.5 | 84.8 |
| Product Yield, % | | | | | | | | | |
| Cyclohexane | 2.2 | 3.2 | 1.8 | 2.0 | 1.6 | 2.6 | 5.0 | 6.3 | 3.9 |
| CHB | 35.6 | 38.7 | 34.5 | 32.3 | 35.5 | 38.7 | 38.6 | 35.0 | 29.1 |
| DCHB | 8.5 | 4.7 | 8.2 | 9.3 | 8.9 | 5.7 | 4.1 | 6.2 | 12.2 |
| CHB + DCHB | 44.1 | 43.4 | 42.7 | 41.6 | 44.4 | 44.4 | 42.6 | 41.2 | 41.3 |

TABLE 6

| Test Condition No. | 29 | 30 | 31 | 32 | 33 | 34 | 35 | 36 |
|---|---|---|---|---|---|---|---|---|
| Sample ID | 71 | 76 | 79 | 83 | 86 | 87 | 91 | 97 |
| Days on Stream | 67.7 | 72.7 | 75.7 | 77.9 | 79.7 | 80.7 | 84.7 | 89.7 |
| Pressure, kPag | 1034 | 1034 | 4137 | 4137 | 4137 | 1034 | 2069 | 2069 |
| Temperature, ° C. | 150 | 150 | 150 | 175 | 175 | 150 | 125 | 125 |
| Pressure, psig | 150 | 150 | 600 | 600 | 600 | 150 | 300 | 300 |
| H2/Benzene Molar Ratio | 1.28 | 0.64 | 0.64 | 1.28 | 0.64 | 0.64 | 0.64 | 0.32 |
| Benzene WHSV | 0.26 | 0.26 | 0.52 | 1.05 | 1.05 | 0.52 | 0.52 | 0.52 |
| Benzene Conv, % | 72.9 | 53.9 | 47.8 | 82.7 | 49.6 | 31.0 | 24.5 | 20.9 |
| Hydrogen Conv, % | 70.2 | 98.5 | 97.9 | 93.8 | 98.2 | 51.5 | 38.6 | 77.6 |
| Selectivity, wt % | | | | | | | | |
| Methylcyclopentane | 0.34 | 0.2 | 0.1 | 0.3 | 0.2 | 0.1 | 0.0 | 0.0 |
| Cyclohexane | 5.6 | 5.1 | 13.0 | 12.6 | 9.6 | 4.2 | 5.8 | 13.3 |
| CHB | 53.0 | 67.1 | 67.1 | 49.0 | 67.3 | 73.8 | 79.0 | 76.5 |
| MCPB | 2.5 | 2.27 | 2.17 | 3.18 | 3.50 | 2.19 | 1.09 | 0.96 |
| DCHB | 32.0 | 21.7 | 15.4 | 27.9 | 15.8 | 16.9 | 12.4 | 8.1 |

TABLE 6-continued

| Test Condition No. | 29 | 30 | 31 | 32 | 33 | 34 | 35 | 36 |
|---|---|---|---|---|---|---|---|---|
| MCP-CHB | 3.4 | 2.5 | 1.8 | 4.2 | 2.9 | 1.9 | 1.2 | 0.8 |
| Others | 3.1 | 1.0 | 0.4 | 2.7 | 0.5 | 0.5 | 0.2 | 0.1 |
| Sum | 100 | 100 | 100 | 100 | 100 | 100 | 100 | 99.8 |
| CHB + DCHB sel, % | 85.0 | 88.8 | 82.5 | 76.9 | 83.2 | 90.8 | 91.4 | 84.7 |
| Product Yield, % | | | | | | | | |
| Cyclohexane | 2.7 | 2.5 | 6.4 | 6.2 | 4.7 | 2.1 | 2.8 | 6.5 |
| CHB | 25.8 | 32.7 | 32.7 | 23.9 | 32.8 | 36.0 | 38.5 | 37.3 |
| DCHB | 15.6 | 10.6 | 7.5 | 13.6 | 7.7 | 8.2 | 6.1 | 4.0 |
| CHB + DCHB | 41.4 | 43.3 | 40.2 | 37.5 | 40.5 | 44.2 | 44.5 | 41.3 |

Figure 2:
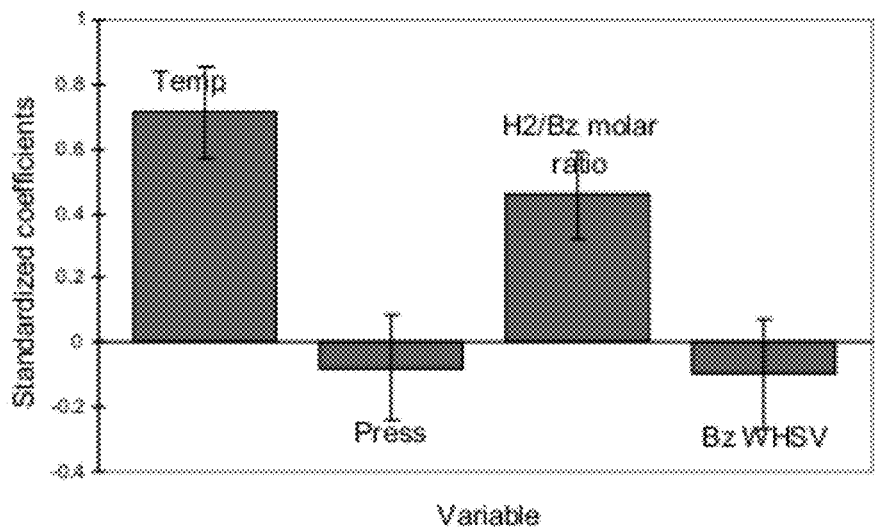
FIGS. 2(a) to (d) are graphs plotting the effect of the process variables temperature, pressure, hydrogen to benzene molar ratio and weight hourly space velocity of benzene on total selectivity to impurities other than CH and DCHB (FIG. 2(a)), methylcyclopentane (MCP) selectivity (FIG. 2(b)), methylcyclopentylbenzene (MCPB) selectivity (FIG. 2(c)), and methylcyclopentyl-cyclohexylbenzene (MCPCHB) selectivity (FIG. 2(d)).
Figure 2:
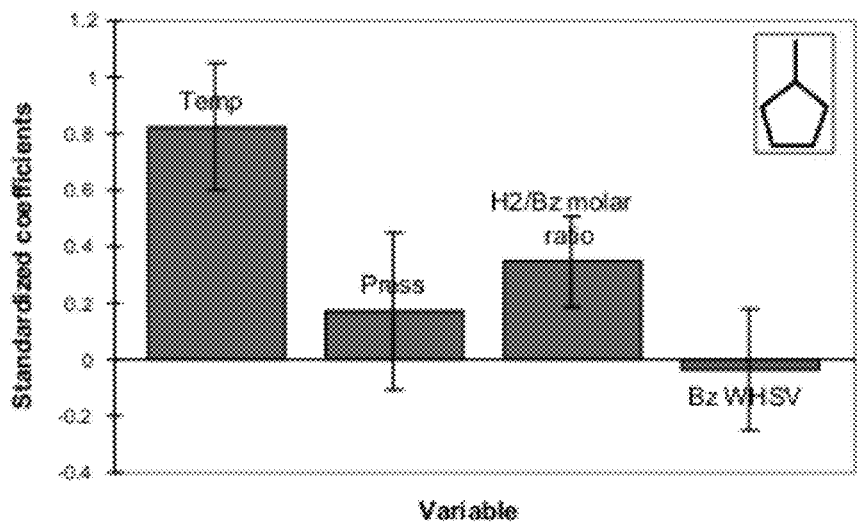
Figure 2:
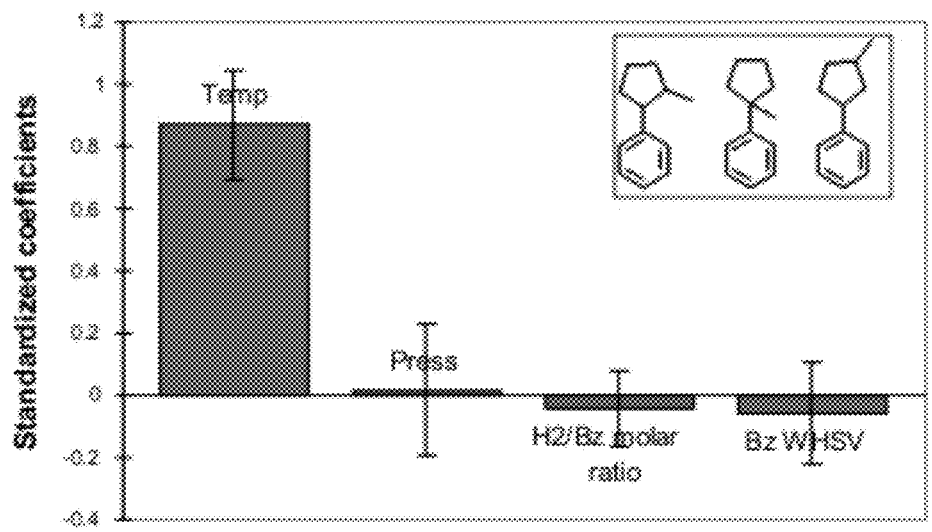
Figure 2D:
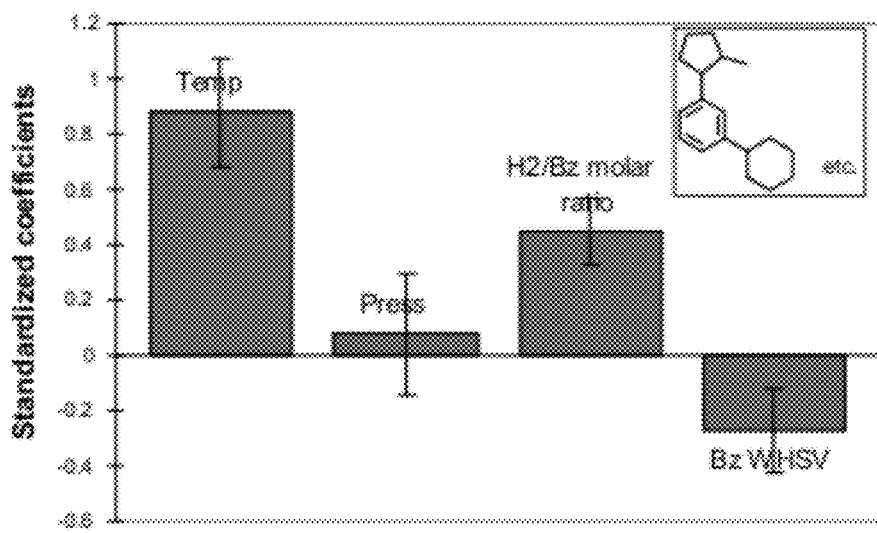

Using the test data in Tables 2 to 5, the effect of process variables on catalyst performance was evaluated. Process variables such as temperature (abbreviated as temp), pressure (abbreviated as press), $H_2$/benzene (Bz) molar ratio, and benzene WHSV were all shown to have a significant effect on catalyst performance. FIG. 1 shows their effect on benzene conversion, and on selectivities to cyclohexane (CH), CHB and DCHB. FIG. 2 shows their effect on the formation of other byproducts such as MCP (methylcyclopentane), MCPB (methylcyclopentyl-benzene), and MCP-CHB (methylcyclopentyl-cyclohexylbenzene). Based on these results, it was possible to show that using an MCM-22 family catalyst and a controlled set of process conditions, cyclohexylbenzene could be produced in high yield and with very low production of undesirable impurities (particularly cyclohexane, MCP, MCPB and MCP-CHB).

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing cyclohexylbenzene, the process comprising contacting benzene and hydrogen under hydroalkylation conditions with a catalyst system comprising a MCM-22 family molecular sieve, an inorganic oxide support different from the molecular sieve and at least one hydrogenation metal, wherein, at least 50 wt % of the hydrogenation metal is supported on the inorganic oxide support, and the conditions comprise a pressure of from 931 kPag to 1207 kPag (135 psig to 175 psig).

2. The process of claim 1, wherein the conditions comprise a pressure of from 1000 kPag to 1069 kPag (145 psig to 155 psig).

3. The process of claim 1, wherein the conditions comprise a temperature of from a temperature of from 140° C. to 175° C.

4. The process of claim 1, wherein the conditions further comprise a hydrogen to benzene molar ratio of from 0.30 to 0.65 and a weight hourly space velocity of benzene of from 0.26 to 1.05 hr$^{-1}$.

5. The process of claim 1, wherein the conditions further comprise a hydrogen to benzene molar ratio of from 0.45 to 0.64 and a weight hourly space velocity of benzene of from 0.3 to 0.6 hr$^{-1}$.

6. The process of claim 1, wherein the MCM-22 family molecular sieve has an X-ray diffraction pattern including d-spacing maxima at 12.4±0.25, 6.9±0.15, 3.57±0.07 and 3.42±0.07 Angstrom.

7. The process of claim 1, wherein the MCM-22 family molecular sieve is selected from MCM-22, PSH-3, SSZ-25, ERB-1, ITQ-1, ITQ-2, MCM-36, MCM-49, MCM-56, UZM-8 and mixtures of any two or more thereof.

8. The process of claim 1, wherein the MCM-22 family molecular sieve is selected from MCM-22, MCM-49, MCM-56 and combinations of any two or more thereof.

9. The process of claim 1, wherein said at least one hydrogenation metal is selected from palladium, ruthenium, nickel, zinc, tin, and cobalt.

10. The process of claim 1, wherein the hydrogenation metal comprises palladium.

11. The process of claim 1, wherein said at least one hydrogenation metal is present in an amount of from 0.05 wt % to 10 wt % based upon the weight of the catalyst system.

12. The process of claim 1, wherein the hydrogenation metal is present in an amount of from 0.1 wt % to 5% wt % based upon the weight of the catalyst system.

13. The process of claim 1, wherein at least 50 wt % of the hydrogenation metal is supported on an inorganic oxide that is different from the molecular sieve.

14. The process of claim 13, wherein at least 75 wt % of the hydrogenation metal is supported on said inorganic oxide.

15. The process of claim 13, wherein substantially all of the hydrogenation metal is supported on said inorganic oxide.

16. The process of claim 13, wherein said inorganic oxide is composited with the molecular sieve, and the hydrogenation metal is applied to the inorganic oxide before the inorganic oxide is composited the molecular sieve.

17. The process of claim 13, wherein the inorganic oxide comprises an oxide of at least one element of Groups 2, 4, 13 and 14 of the Periodic Table of Elements.

18. The process of claim 13, wherein the inorganic oxide comprises alumina and/or titania and/or zirconia.

19. The process of claim 1, which results in an effluent comprising the cyclohexylbenzene product that also contains dicyclohexylbenzene and at least part of the dicyclohexylbenzene is contacted with benzene under transalkylation conditions to produce further cyclohexylbenzene.

20. The process of claim 1, wherein the hydroalkylation conditions are selected to produce a total hydroalkylation effluent containing no more than 3 wt % of cyclohexane and/or no more than 5 wt % of methylcyclopentane, methylcyclopentylbenzene and methylcyclopentyl-cyclohexylbenzene in combination.

21. A method for coproducing phenol and cyclohexanone, the method comprising producing cyclohexylbenzene by the process of claim 1, oxidizing the cyclohexylbenzene to produce cyclohexylbenzene hydroperoxide, and cleaving the cyclohexylbenzene hydroperoxide to produce phenol and cyclohexanone.

* * * * *